United States Patent [19]
Armistead

[11] Patent Number: 6,037,370
[45] Date of Patent: Mar. 14, 2000

[54] METHODS AND COMPOSITIONS FOR STIMULATING NEURITE GROWTH

[75] Inventor: David M. Armistead, Maynard, Mass.

[73] Assignee: Vertex Pharmaceuticals Incorporated, Cambridge, Mass.

[21] Appl. No.: 08/486,004

[22] Filed: Jun. 8, 1995

[51] Int. Cl.$^7$ ............... A61K 31/235; A61K 31/24; A61K 31/40; A61K 31/38

[52] U.S. Cl. ............ 514/533; 514/534; 514/330; 514/423; 514/428; 514/438; 514/538; 514/547; 514/549; 514/551; 514/465; 514/466

[58] Field of Search ............... 514/533, 534, 514/330, 423, 428, 438, 538, 547, 548, 551, 465, 466

[56] References Cited

U.S. PATENT DOCUMENTS

| | | | |
|---|---|---|---|
| 5,330,993 | 7/1994 | Armistead et al. | 514/330 |
| 5,614,547 | 3/1997 | Hamilton et al. | 514/423 |

FOREIGN PATENT DOCUMENTS

| | | |
|---|---|---|
| WO 93/00427 | 1/1993 | WIPO . |
| WO 94/07858 | 4/1994 | WIPO . |
| WO 96/40140 | 12/1996 | WIPO . |

OTHER PUBLICATIONS

J.R. Hauske et al., "Design and synthesis of novel FKBP inhibitors," *J. Med. Chem.*, 35, pp. 4284–4296 (1992).

W.E. Lyons et al., "Immunosupressant FK506 promotes neurite outgrowth in cultures of PC12 cells and sensory gaglia," *Proc. Natl. Acad. Sci. USA*, 91, pp. 3191–3195 (Apr., 1994).

W.E. Lyons et al., "Neuronal regeneration enhances the expression of the immunophilin FKBP–12," *J. Neuroscience.*, 15, pp. 2985–2994 (Apr., 1995).

B.G. Gold et al., "FK506, an immunosuppressant, increases functional recovery and axonal regeneration in the rat following axotomy of the sciatic nerve," *Soc. Neurosci. Abs.*, 19, p. 1316 (1993).

*Primary Examiner*—Theodore J. Criares
*Attorney, Agent, or Firm*—Fish & Neave; James F. Haley, Jr.; Andrew S. Marks

[57] ABSTRACT

The present invention relates to methods and pharmaceutical compositions for stimulating the growth of neurites in nerve cells. The compositions comprise a neurotrophic amount of a compound which binds to the FK-506 binding protein (FKBP) and a neurotrophic factor, such as nerve growth factor NGF. The methods comprise treating nerve cells with the above-described compositions or compositions comprising the FKBP binding compound without a neurotrophic factor. The methods of this invention can be used to promote repair of neuronal damage caused by disease or physical trauma.

11 Claims, No Drawings

METHODS AND COMPOSITIONS FOR STIMULATING NEURITE GROWTH

TECHNICAL FIELD OF THE INVENTION

The present invention relates to methods and pharmaceutical compositions for stimulating the growth of neurites in nerve cells. The compositions comprise a neurotrophic amount of a compound which binds to the FK-506 binding protein (FKBP) and a neurotrophic factor, such as nerve growth factor NGF. The methods comprise treating nerve cells with the above-described compositions or compositions comprising the FKBP binding compound without a neurotrophic factor. The methods of this invention can be used to promote repair of neuronal damage caused by disease or physical trauma.

BACKGROUND OF THE INVENTION

Immunophilins are a family of soluble proteins that mediate the actions of immunosuppressant drugs such as cyclosporin A, FK506 and rapamycin. Of particular interest is the 12 kDa immunophilin, FK-506 binding protein (FKBP12). FKBP12 binds FK-506 and rapamycin, leading to an inhibition of T-cell activation and proliferation. Interestingly, the mechanism of action of FK-506 and rapamycin are different. For review, see, S. H. Solomon et al., *Nature Med.*, 1, pp. 32–37 (1995).

FK-506 binds to FKBP12 and the resulting complex binds to and inhibits calcineurin, a cytoplasmic phosphatase. The phosphatase activity of calcineurin is necessary for dephosphorylation and subsequent translocation into the nucleus of the transcription factor NF-AT. NF-AT causes interleukin-2 gene activation which in turn mediates T-cell proliferation.

The rapamycin-FKBP12 complex, on the other hand, associates with a protein of unknown function, termed RAFT1/FRAP. This tripartite complex is known to inhibit various kinases in the cell (i.e., p70S6, p34cdc2, cdk2) which are necessary for cell cycle progression in T-cells. Rapamycin is also known to be a potent antagonist of FK-506, presumably by acting as a competitive inhibitor for the FKBP12 binding.

More recently, it has been discovered that FKBP plays other important roles in the body. It has been found that FKBP12 forms a complex with the intracellular calcium ion channels—the ryanodine receptor (RyR) and the inositol 1,4,5-triphosphate receptor (IP$_3$R) [T. Jayaraman et al., *J. Biol. Chem.*, 267, pp. 9474–77 (1992); A. M. Cameron et al., *Proc. Natl. Acad. Sci. USA*, 92, pp. 1784-44 (1995)], helping to stabilize calcium release. The ryanodine receptor has been found in skeletal muscle, cardiac muscle, brain and other excitable tissues. IP$_3$R mediates intracellular calcium release elicited by hormones and neurotransmitters that act at the cell surface to activate phospholipase C and generate inositol 1,4,5-triphophase (IP$_3$). Most IP$_3$R is found associated with the endoplasmic reticulum, but some may occur on the cell surface and mediate calcium flux into the cell.

For both the RyR and the IP$_3$R, it has been demonstrated that FK506 and rapamycin are capable of dissociating FKBP12 from the receptor. In each case, the "stripping" off of FKBP12 leads to increased leakiness of the calcium channel and lower intracellular calcium concentrations.

Another role of FKBP12 is the regulation of neurite outgrowth in nerve cells. W. E. Lyons et al. [*Proc. Natl. Acad. Sci. USA*, 91, pp. 3191–95 (1994)] demonstrated that FK506 acts synergistically with nerve growth factor (NGF) in stimulating neurite outgrowth in a rat pheochromocytoma cell line. Interestingly, rapamycin did not inhibit the effects of FK-506 on neurite outgrowth, but rather was neurotrophic itself, displaying an additive effect with FK-506. In sensory ganglia, FK-506 demonstrated similar neurotrophic effects, but those effects were blocked by rapamycin. These results led the authors to speculate that FK-506 was exerting its neurotrophic effect through its complexing with FKBP12 and calcineurin and inhibition of the latter's phosphatase activity. Alternatively, the authors proposed FK-506 was acting via a "stripping" mechanism, such as that involved in the removal of FKBP12 from RyR and IP$_3$R.

In view of the wide variety of disorders that may be treated by stimulating neurite outgrowth and the relatively few FKBP12-binding compounds that are known to possess this property, there remains a great need for additional neurotrophic, FKBP12-binding compounds.

SUMMARY OF THE INVENTION

Applicant has solved the problem referred to above by discovering that two genera of novel FKBP12-binding compounds he had previously co-invented also possess neurotrophic activity. Applicant had previously described a series of acylated amino acid derivatives which bind to FKBP12 in PCT patent publications WO 92/19593 and WO 94/07858. Another series of FKBP12 ligands are described in applicant's U.S. Pat. Nos. 5,192,773 and 5,330,993 and PCT patent publication WO 92/00278. Each series of compounds stimulate neurite outgrowth in the presence of exogenous or endogenous NGF.

The compositions provided comprise a compound from one of the two genera described above and a neuronal growth factor. The methods described herein employ those previously described compounds and compositions comprising them to effectuate neurite outgrowth are useful to treat nerve damage caused by various diseases and physical traumas.

DETAILED DESCRIPTION OF THE INVENTION

According to one embodiment, the present invention provides pharmaceutical compositions which comprise:

a) a compound with affinity for FKBP12 having the formula (I):

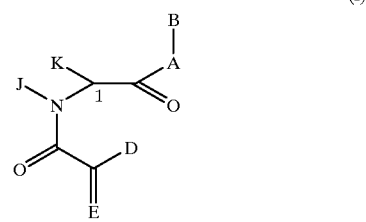

and pharmaceutically acceptable derivatives thereof,
wherein A in O, NH, or N-(C1–C4 alkyl);
wherein B is hydrogen, CHL-Ar, (C1–C6)-straight or branched alkyl, (C2–C6)-straight or branched alkenyl, (C5–C7)-cycloalkyl, (C5–C7)-cycloalkenyl or Ar substituted (C1–C6)-alkyl or (C2–C6)-alkenyl, or

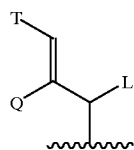

wherein L and Q are independently hydrogen, (C1–C6)-straight or branched alkyl or (C2–C6)-straight or branched alkenyl;

wherein T is Ar or substituted cyclohexyl with substituents at positions 3 and 4 which are independently selected from the group consisting of hydrogen, hydroxyl, O-(C1–C4)-alkyl or O-(C2–C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1–C6)-straight or branched alkyl or (C2–C6)-straight or branched alkenyl, O-(C1–C4)-straight or branched alkyl or O-((C2–C4)-straight or branched alkenyl), O-benzyl, O-phenyl, amino and phenyl;

wherein D is U; E is either oxygen or CH—U, provided that if D is hydrogen, then E is CH—U or if E is oxygen then D is not hydrogen;

wherein each U is independently selected from hydrogen, O-(C1–C4)-straight or branched alkyl or O-((C2–C4)-straight or branched alkenyl), (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, 2-indolyl, 3-indolyl, [(C1–C4)-alkyl or (C2–C4)-alkenyl]-Ar or Ar;

wherein J is hydrogen or C1 or C2 alkyl; K is (C1–C4)-straight or branched alkyl, benzyl or cyclohexylmethyl; or wherein J and K may be taken together to form a 5–7 membered heterocyclic ring which may contain an O, S, SO or $SO_2$ substituent therein;

wherein the stereochemistry at carbon position 1 is R or S;

b) a neurotrophic factor; and c) a pharmaceutically suitable carrier.

More preferably, in the compound with affinity for FKBP12 in these pharmaceutical compositions: A is oxygen; J is hydrogen or C1 or C2 alkyl; K is (C1–C4)-straight or branched alkyl, benzyl or cyclohexylmethyl; or J and K are taken together to form pyrrolidyl or piperidyl; and the stereochemistry at carbon position 1 is S.

In the above preferred compounds wherein J and K are taken together to form pyrrolidyl or piperidyl and E is CH—U, U is preferably dimethylaminophenyl, methoxyphenyl, dimethoxyphenyl, trimethoxyphenyl, nitrophenyl, furyl, indolyl, pyridyl, or methylenedioxyphenyl.

In the above preferred compounds wherein J and K are taken together to form pyrrolidyl or piperidyl and E is oxygen:

B is preferably benzyl, naphthyl, tert-butyl, hydrogen, E-3-phenyl-2-methyl-prop-2-enyl, E-3-(4-hydroxyphenyl) 2-methyl-prop-2-enyl, E-3-[trans(4-hydroxycyclohexyl)]-2-methyl-prop-2-enyl, cyclohexylethyl, cyclohexylpropyl, cyclohexylbutyl, cyclopentylopropyl, E-3-(4-methoxyphenyl)-2-methyl-prop-2-enyl, E-3-(3,4-dimethoxyphenyl)-2-methyl-prop-2-enyl or E-3-[cis(4-hydroxycyclohexyl)]-2-methyl-prop-2-enyl; and D is preferably phenyl, methoxyphenyl, cyclohexyl, ethyl, methoxy, nitrobenzyl, thiophenyl, indolyl, furyl, pyridyl, pyridyl-N-oxide, nitrophenyl, fluorophenyl, trimethoxyphenyl or dimethoxyphenyl.

The most preferred compounds of formula (I) useful in the compositions and methods of this invention are those of formulae Ia, Ib, Ic and Id, listed in Tables 1a through 1d, respectively, set forth in Example 1, below.

The synthesis of compounds of formula (I) with affinity for FKBP12 in these compositions is described in U.S. Pat. Nos. 5,192,773 and 5,330,993 and PCT patent publication WO 92/00278, the disclosures of which are herein incorporated by reference.

According to an alternate embodiment, the present invention provides pharmaceutical compositions which comprise:

a) a compound with affinity for FKBP12 having the formula (II):

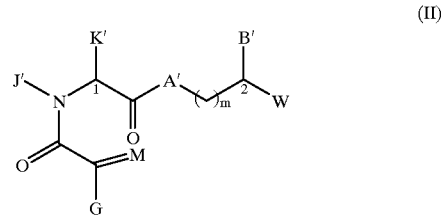

and pharmaceutically acceptable derivatives thereof, wherein A' is $CH_2$, oxygen, NH or N-(C1–C4 alkyl); wherein B' and W are independently:

(i) hydrogen, Ar', (C1–C10)-straight or branched alkyl, (C2–C10)-straight or branched alkenyl or alkynyl, (C5–C7)-cycloalkyl substituted (C1–C6)-straight or branched alkyl, (C2–C6)-straight or branched alkenyl or alkynyl, (C5–C7)-cycloalkenyl substituted (C1–C6)-straight or branched alkyl, (C2–C6)-straight or branched alkenyl or alkynyl, or Ar' substituted (C1–C6)-straight or branched alkyl, (C2–C6)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$, N, and NR, wherein R is selected from the group consisting of hydrogen, (C1–C4)-straight or branched alkyl, (C2–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar' group; or

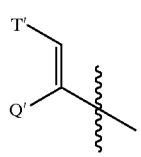

wherein Q' is hydrogen, (C1–C6)-straight or branched alkyl or (C2–C6)-straight or branched alkenyl or alkynyl;

wherein T' is Ar' or substituted 5–7 membered cycloalkyl with substituents at positions 3 and 4 which are independently selected from the group consisting of oxo, hydrogen, hydroxyl, O-(C1–C4)-alkyl, and O-(C2–C4)-alkenyl;

wherein Ar' is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar' may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O-[(C1–C4)-straight or branched alkyl], O-[(C2–C4)-straight or branched alkenyl], O-benzyl, O-phenyl, 1,2-methylenedioxy, amino, carboxyl, N-[(C1–C5)-straight or branched alkyl or (C2–C5)-straight or branched alkenyl) carboxamides, N,N-di-[(C1–C5)-straight or branched alkyl or (C2–C5)-straight or branched alkenyl)]carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and q is 0–2;

wherein G is U';

M is either oxygen or CH—U'; provided that if G is hydrogen, then M is CH—U' or if M is oxygen, then G is U';

wherein U' is hydrogen, O-[(C1–C4)-straight or branched alkyl] or O-[(C2–C4)-straight or branched alkenyl], (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]-Y or Y;

wherein Y is selected from the group consisting of phenyl, 1-naphthyl, 2-naphthyl, indenyl, azulenyl, fluorenyl, anthracenyl, 2-pyrrolinyl, 3-pyrrolinyl, pyrolidinyl, 1,3-dioxolyl, 2-imidazolinyl, imidazolidinyl, 2H-pyranyl, 4H-pyranyl, piperidyl, 1,4-dioxanyl, morpholinyl, 1,4-dithianyl, thiomorpholinyl, piperazinyl, quinuclidinyl, and heterocyclic aromatic groups as defined for Ar' above;

wherein Y may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O-[(C1–C4)-straight or branched alkyl], O-[(C2–C4)-straight or branched alkenyl], O-benzyl, O-phenyl, 1,2-methylenedioxy, amino, and carboxyl;

wherein J' is hydrogen, (C1–C2) alkyl or benzyl;

K is (C1–C4)-straight or branched alkyl, benzyl or cyclohexylmethyl, or wherein J' and K may be taken together to form a 5–7 membered heterocyclic ring which may contain a heteroatom selected from the group consisting of O, S, SO and SO$_2$; and wherein m is 0–3;

b) a neurotrophic factor; and c) a pharmaceutically suitable carrier. The compounds of formula (II) exclude any compounds of formula (I).

More preferably, in the compound with affinity for FKBP12 in these pharmaceutical compositions:

B' and W are independently:

(i) hydrogen, Ar', (C1–C10)-straight or branched alkyl, (C2–C10)-straight or branched alkenyl or alkynyl, (C5–C7)-cycloalkyl substituted (C1–C6)-straight or branched alkyl, (C2–C6)-straight or branched alkenyl or alkynyl, (C5–C7)-cycloalkenyl substituted (C1–C6)-straight or branched alkyl, (C2–C6)-straight or branched alkenyl or alkynyl, or Ar' substituted (C1–C6)-straight or branched alkyl, (C2–C6)-straight or branched alkenyl or alkynyl wherein, in each case, any one of the CH$_2$ groups of said alkyl, alkenyl or alkynyl chains may be optionally replaced by a heteroatom selected from the group consisting of O, S, SO, SO$_2$; or

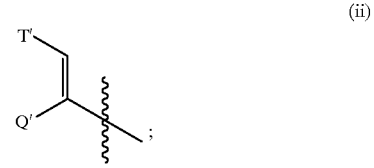

Ar' may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O-[(C1–C4)-straight or branched alkyl], O-[(C2–C4)-straight or branched alkenyl], O-benzyl, O-phenyl, 1,2-methylenedioxy, amino and carboxyl; and Y is selected from the group consisting of phenyl, 1-naphthyl, 2-naphthyl, indenyl, azulenyl, fluorenyl, anthracenyl and heterocyclic aromatic groups as defined for Ar' above.

According to other preferred embodiments, in the compound with affinity for FKBP12 having the formula (II):

at least one of B' or W is independently selected from the group consisting of (C2–C10)-straight or branched alkynyl; (C5–C7)-cycloalkyl substituted (C2–C6)-straight or branched alkynyl; (C5–C7)-cycloalkenyl substituted (C2–C6)-straight or branched alkynyl; and Ar' substituted (C2–C6)-straight or branched alkynyl.

Alternatively, at least one of B' or W is independently represented by the formula $-(CH_2)_r-(Z)-(CH_2)_s-Ar'$, wherein:

Z is independently selected from the group consisting of $CH_2$, O, S, SO, $SO_2$, N, and NR;

r is 0–4;

s is 0–1; and

Ar' and R are as defined above in formula II.

In yet another alternative embodiment of formula II, at least one of B' or W is independently selected from the group consisting of Ar', Ar'-substituted (C1–C6)-straight or branched alkyl, and Ar'-substituted (C2–C6)-straight or branched alkenyl or alkynyl;

wherein Ar' is substituted with one to three substituents which are independently selected from the group consisting of N-(straight or branched (C1–C5)-alkyl or (C2–C5)-alkenyl) carboxamides, N,N-di-(straight or branched (C1–C5)-alkyl or (C2–C5)-alkenyl) carboxamides, N-morpholinocarboxamide, N-benzylcarboxamide, N-thiomorpholinocarboxamide, N-picolinoylcarboxamide, O—X, $CH_2-(CH_2)_q-X$, $O-(CH_2)_q-X$, $(CH_2)_q-O-X$, and CH=CH—X; and Ar', X and q are as defined above.

Most preferably, the compounds of formula (II) used in the pharmaceutical compositions are selected from those of formula (II') listed in Table 2, set forth in Example 1.

The synthesis of compounds of formula II is described in detail in applicant's PCT patent publications WO 92/19593 and WO 94/07858, the disclosures of which are herein incorporated by reference.

As used herein, the FKBP12 binding compounds used in the pharmaceutical compositions and methods of this invention, are defined to include pharmaceutically acceptable derivatives thereof. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote or augment neurite outgrowth.

If pharmaceutically acceptable salts of the FKBP12 binding compounds are used, those salts are preferably derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The FKBP12 binding compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The neurotrophic activity of the FKBP12 binding compounds of this invention is directly related to their affinity for FKBP12 and their ability to inhibit FKBP12 rotomase activity. In order to quantitate these properties, several assays known in the art may be employed. For example, competitive LH20 binding assays using labelled FK-506 as a reporting ligand have been described by M. W. Harding et al., *Nature*, 341, pp. 758–60 (1989) and by J. J. Siekierka et al., Nature, 341, pp. 755–57 (1989).

Preferably, the assay measures inhibition of FKBP12 rotomase activity. Such an assay has also been described by M. W. Harding et al., supra and by J. J. Siekierka et al., supra. In this assay the isomerization of an artificial substrate—N-succinyl-Ala-Ala-Pro-Phe-p-nitroanilide—is followed spectrophotometrically. The assay includes the cis form of the substrate, FKBP12, the inhibitor and chymotrypsin. Chymotrypsin is able to cleave p-nitroanilide from the trans form of the substrate, but not the cis form. Release of p-nitroanilide is measured.

The second component in each of the pharmaceutical compositions described above is a neurotrophic factor. The term "neurotrophic factor", as used herein, refers to compounds which are capable of stimulating growth or proliferation of nervous tissue. As used in this application, the term "neurotrophic factor" excludes the FKBP12 binding compounds described herein, as well as FK-506 and rapamycin.

Numerous neurotrophic factors have been identified in the art and any of those factors may be utilized in the compositions of this invention. These neurotrophic factors include, but are not limited to, nerve growth factor (NGF), insulin growth factor (IGF-1) and its active truncated derivatives such as gIGF-1, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3)and neurotrophin 4/5 (NT-4/5). The most preferred neurotrophic factor in the compositions of this invention is NGF.

The third component of the pharmaceutically acceptable compositions of this invention is a pharmaceutically acceptable carrier. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both FKPB12 binding compound and the neurotrophic factor that may be combined with the carrier materials to produce a single dosage form will vary depending upon the host treated, the particular mode of administration. The two active ingredients of the pharmaceutical compositions of this invention act synergistically to stimulate neurite outgrowth. Therefore, the amount of neurotrophic factor in such compositions will be less than that required in a monotherapy utilizing only that factor. Preferably, the compositions should be formulated so that a dosage of between 0.01–100 mg/kg body weight/day of the FKBP12 binding protein can be administered and a dosage of between 0.01–100 $\mu$g/kg body weight/day of the neurotrophic can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular FKBP12 binding compound and neurotrophic factor in the composition.

According to another embodiment, this invention provides methods for stimulating neurite outgrowth. Such methods comprise the step of treating nerve cells with any of the FKBP12 binding compounds described above. Preferably, this method is used to stimulate neurite outgrowth in a patient and the FKBP12 binding compound is formulated into a composition additionally comprising a pharmaceutically acceptable carrier. The amount of FKBP12 binding compound utilized in these methods is between about 0.01 and 100 mg/kg body weight/day.

According to an alternate embodiment, the method of stimulating neurite outgrowth comprises the additional step of treating nerve cells with a neurotrophic factor, such as those contained in the pharmaceutical compositions of this invention. This embodiment includes administering the FKBP12 binding compound and the neurotrophic agent in a single dosage form or in separate, multiple dosage forms. If separate dosage forms are utilized, they may be administered concurrently, consecutively or within less than about 5 hours of one another.

Preferably, the methods of this invention is used to stimulate neurite outgrowth in a patient.

The methods and compositions of this invention may be used to treat nerve damage caused by a wide variety of diseases or physical traumas. These include, but are not limited to, Alzheimer's disease, Parkinson's disease, ALS, stroke and ischemia associated with stroke, neural paropathy, other neural degenerative diseases, motor neuron diseases, sciatic crush, spinal cord injuries and facial nerve crush.

In order that the invention described herein may be more fully understood, the following examples are set forth. It should be understood that these examples are for illustrative purposes only and are not to be construed as limiting this invention in any manner.

EXAMPLE 1

FKBP12 Binding Assay

The inhibition of FKBP rotomase activity by the preferred FKBP12 binding compounds present in the compositions of this invention was assayed. In this assay various quantities of FKBP12 binding compound (0.1 nM–10 μM) were added to cis-N-succinyl-Ala-Ala-Pro-Phe-p-nitroanilide in the presence of FKBP12 and chymotrypsin. FKBP12 converts the cis form of the substrate to the trans form. This allows chymotrypsin to cleave p-nitroanilide from the substrate. Release of p-nitroanilide was measured spectrophotometrically. This assay allowed me to measure the change in the first order rate constant of the rotomase activity as a function of FKBP12 binding compound concentration and yielded an estimate of apparent $K_i$. The most preferred FKBP12 binding compounds utilized in the compositions and methods of this invention and their calculated $K_i$ are tabulated below.

TABLE 1a (formula Ia)

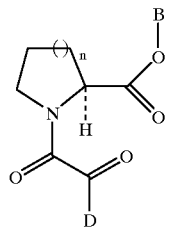

| B | D | n | $K_i$ (μM) |
|---|---|---|---|
| Benzyl | Phenyl | 1 | 25 |
| Benzyl | Phenyl | 2 | 1.5 |
| Allyl | Phenyl | 2 | 8 |
| 1-Naphthyl | Phenyl | 2 | 0.9 |
| 2-Naphthyl | Phenyl | 2 | 7 |
| Benzyl | 2-Methylpropyl | 2 | 0.9 |
| Benzyl | 2-Methoxyphenyl | 2 | 17 |
| Benzyl | 3-Methoxyphenyl | 2 | 0.3 |
| Benzyl | 4-Methoxyphenyl | 2 | 5 |
| Benzyl | 3,5-Dimethoxyphenyl | 2 | 2 |
| Benzyl | 2,6-Dimethoxyphenyl | 2 | 50 |
| Benzyl | 3,4,5-Trimethoxyphenyl | 2 | 0.1 |
| Benzyl | 4-Fluorophenyl | 2 | 4 |
| Benzyl | 3-Nitrophenyl | 2 | 160 |
| Benzyl | 4-Nitrophenyl | 2 | 160 |
| Benzyl | 2-Pyridyl | 2 | 130 |
| Benzyl | 2-pyridyl N-oxide | 2 | >500 |
| tert-Butyl | 2-Furyl | 1 | 200 |
| Benzyl | 2-Furyl | 2 | 3 |
| Benzyl | 3-Indoyl | 2 | 25 |
| Benzyl | 2-Thiophenyl | 2 | 0.8 |
| E-3-Phenyl-2-methyl-prop-2-enyl | Phenyl | 2 | 1.5 |
| E-3-(4-Hydroxyphenyl)-2-methyl-prop-2-enyl | Phenyl | 2 | 6 |
| E-3-[cis-(4-Hydroxycyclohexyl)]-2-methyl-prop-2-enyl | Phenyl | 2 | 0.6 |
| E-3-[trans-(4-Hydroxycyclohexyl)]-2-methyl-prop-2-enyl | Phenyl | 2 | 0.5 |
| Benzyl | 2-Nitrobenzyl | 2 | 26 |
| Hydrogen | Methoxy | 2 | ND |
| tert-Butyl | Methoxy | 1 | 600 |
| Allyl | Methoxy | 2 | 190 |

TABLE 1a-continued (formula Ia)

| B | D | n | $K_i$ ($\mu M$) |
|---|---|---|---|
| Benzyl | Methoxy | 2 | 80 |
| 2-Cyclohexylethyl | Methoxy | 2 | 45 |
| 3-Cyclohexylpropyl | Methoxy | 2 | 20 |
| 4-Cyclohexylbutyl | Methoxy | 2 | 6 |
| 3-Cyclopentylpropyl | Methoxy | 2 | 35 |
| E-3-(4-Methoxyphenyl)-2-methyl-prop-2-enyl | Methoxy | 2 | 40 |
| E-3-(3,4-Dimethoxyphenyl)-2-methyl-prop-2-enyl | Methoxy | 2 | 10 |
| E-3-(4-Hydroxyphenyl)-2-methyl-prop-2-enyl | Methoxy | 2 | 60 |
| E-3-[cis-(4-Hydroxycyclohexyl)]-2-methyl-prop-2-enyl | Methoxy | 2 | 70 |
| Benzyl | Cyclohexyl | 2 | 1.3 |
| Benzyl | Ethyl | 1 | 400 |
| Benzyl | 3-Methoxyphenyl | 1 | 5 |
| Benzyl | 2-Pyridyl | 1 | 300 |
| Benzyl | 3,4-Difluorophenyl | 2 | 3 |
| Benzyl | (E)-2-(4-Methoxyphenyl)-ethenyl | 2 | 1 |
| Benzyl | 1-Hydroxy-1-cyclohexyl | 2 | 1 |
| Benzyl | 2-Naphthyl | 2 | 1.5 |
| Benzyl | 1-Naphthyl | 2 | 1 |
| (S)-alpha-Methylbenzyl | Phenyl | 2 | 0.5 |
| Benzyl | 2-Hydroxy-2-tetrahydropyranyl | 2 | 12 |
| (R)-alpha-Methylbenzyl | Phenyl | 2 | 1.5 |
| Benzyl | 3-Trifluoromethylphenyl | 2 | 1.5 |
| Benzyl | 3-Benzyloxyphenyl | 2 | 0.5 |
| Benzyl | (E)-2-tert-Butylethenyl | 2 | 9 |
| Benzyl | 2-Trifluoromethylphenyl | 2 | 5 |
| 4-Cyclohexylbutyl | Phenyl | 2 | 0.4 |
| 4-Cyclohexylbutyl | 3,4,5-Trimethoxyphenyl | 2 | 0.04 |
| 4-Phenylbenzyl | Phenyl | 2 | 5 |
| 4-Phenylbenzyl | 3,4,5-Trimethoxyphenyl | 2 | 2 |
| Benzyl | 3-Ethoxyphenyl | 2 | 0.56 |
| 3-Phenoxybenzyl | 3,4,5-Trimethoxyphenyl | 2 | 0.018 |
| 3-Phenoxybenzyl | Phenyl | 2 | 0.09 |
| 4-Phenylbutyl | 3,4,5-Trimethoxyphenyl | 2 | 0.019 |
| 4-Phenylbutyl | Phenyl | 2 | 0.35 |
| Benzyl | 3-(3-Propenyloxy)phenyl | 2 | 1 |
| Benzyl | 3-(2-Propoxy)phenyl | 2 | 0.5 |
| Benzyl | 1-Methylpropyl | 2 | 1 |
| 2-Phenylethyl | Phenyl | 2 | 1.1 |
| 6-Phenylhexyl | Phenyl | 2 | 0.5 |
| 5-Phenylpentyl | 3,4,5-Trimethoxyphenyl | 2 | 0.07 |
| 6-Phenylhexyl | 3,4,5-Trimethoxyphenyl | 2 | 0.1 |
| 6-Cyclohexylhexyl | 3,4,5-Trimethoxyphenyl | 2 | 0.05 |
| 4-Phenoxybenzyl | 3,4,5-Trimethoxyphenyl | 2 | 0.8 |
| 5-Cyclohexylpentyl | 3,4,5-Trimethoxyphenyl | 2 | 0.09 |
| Benzyl | 3-(1-Butoxy)phenyl | 2 | 0.36 |
| 4-Phenylbutyl | 3-(2-Propoxy)phenyl | 2 | 0.1 |
| 4-(4-Iodophenyl)butyl | 3,4,5-Trimethoxyphenyl | 2 | 0.016 |
| 4-Iodobenzyl | 3,4,5-Trimethoxyphenyl | 2 | 1.4 |
| 2-(2-Naphthyl)ethyl | 3,4,5-Trimethoxyphenyl | 2 | 0.22 |
| 2-(1-Naphthyl)ethyl | 3,4,5-Trimethoxyphenyl | 2 | 0.5 |
| 4-Phenylbutyl | 4-Iodophenyl | 2 | 0.8 |
| 4-Phenylbutyl | 3-Iodophenyl | 2 | 0.13 |
| 3-Phenylpropyl | 3,4,5-Trimethoxyphenyl | 2 | 0.11 |
| 3-(3-Indolyl)propyl | 3,4,5-Trimethoxyphenyl | 2 | 0.017 |
| 4-(4-Methoxyphenyl)butyl | 3,4,5-Trimethoxyphenyl | 2 | 0.013 |
| 4-Phenylbut-2-enyl | 3,4,5-Trimethoxyphenyl | 2 | 0.8 |
| 4-Phenylbut-3-enyl | 3,4,5-Trimethoxyphenyl | 2 | 0.5 |
| 4-(4-Allocaminophenyl)propyl | 3,4,5-Trimethoxyphenyl | 2 | 0.011 |
| 4-Phenylpropyl | 1-Cyclohexenyl | 2 | 0.78 |

TABLE 1a-continued (formula Ia)

| B | D | n | $K_i$ (μM) |
|---|---|---|---|
| 4-(4-Methoxyphenyl)but-3-eny | 3,4,5-Trimethoxyphenyl | 2 | 0.011 |
| 4-Phenylpropyl | 1-Fluoro-1-cyclohexyl | 2 | 0.54 |
| 4-Phenylpropyl | 3-Butoxyphenyl | 2 | 1.4 |
| 3-[3-(N-Formylindolyl)]propyl | 3,4,5-Trimethoxyphenyl | 2 | 0.015 |
| 4-(3-indolyl)butyl | 3,4,5-Trimethoxyphenyl | 2 | 0.016 |
| 4-Phenylbutyl | Benzyl | 2 | 0.35 |
| 4-Phenylbutyl | 3-Biphenyl | 2 | 0.04 |
| 4-Phenylbutyl | 4-tert-Butylphenyl | 2 | 0.6 |
| 4-Phenylbutyl | Cyclohexyl | 2 | 0.08 |
| 4-Phenylbutyl | Cyclohexylmethyl | 2 | 0.12 |
| 4-Phenylbutyl | 3,4-Methylenedioxyphenyl | 2 | 0.25 |
| 4-Phenylbutyl | 4-Tetrahydropyranyl | 2 | 0.44 |
| 4-Phenylbutyl | 3-Cyclohexyl-4-methoxy-phenyl | 2 | 14 |
| 4-Phenylbutyl | 4-(4-Methoxybenzyloxy-methyl)-2-furyl | 2 | 0.7 |
| 4-Phenylbutyl | tert-Butyl | 2 | 0.18 |
| 4-Phenylbutyl | Ethyl | 2 | 1.6 |
| 3-(N-Benzimidazolyl)propyl | 3,4,5-Trimethoxyphenyl | 2 | 0.11 |
| 3-(N-Purinyl)propyl | 3,4,5-Trimethoxyphenyl | 2 | 0.13 |
| (S,S)-2-Methyl-3-hydroxy-4-phenylpropyl | 3,4,5-Trimethoxyphenyl | 2 | 0.25 |

TABLE 1b (formula 1b)

| B | U | n | $K_i$ |
|---|---|---|---|
| Benzyl | 3,4-Methylenedioxyphenyl | 1 | 3 |
| Benzyl | 3,4-Methylenedioxyphenyl | 2 | 3 |
| Benzyl | 4-Methoxyphenyl | 1 | 6 |
| Benzyl | 4-Methoxyphenyl | 2 | 4 |
| Benzyl | 2,5-Dimethoxyphenyl | 1 | 10 |
| Benzyl | 2,4,5-Trimethoxyphenyl | 1 | 25 |
| Benzyl | 3,4,5-Trimethoxyphenyl | 1 | 450 |
| Benzyl | 4-Dimethylaminophenyl | 2 | 20 |
| Benzyl | 4-Nitrophenyl | 2 | 14 |
| Benzyl | 1-Furyl | 2 | 2.5 |
| Benzyl | 2-Furyl | 2 | 2.5 |
| Benzyl | 3-Indoyl | 2 | >60 |
| Benzyl | 3-Pyridyl | 2 | 25 |
| Benzyl | Hydrogen | 2 | 300 |
| Benzyl | Phenyl | 2 | 11 |

TABLE 1c (formula Ic)

| B | D | J | K | $K_i$ (μM) |
|---|---|---|---|---|
| Benzyl | Methoxy | Methyl | Hydrogen | 1000 |
| Benzyl | Methoxy | Methyl | S-methyl | 400 |
| Benzyl | Methoxy | Methyl | S-Isopropyl | 170 |
| Ethyl | Methoxy | Benzyl | Hydrogen | >1200 |
| tert-Butyl | Methoxy | Ethyl | S-Methyl | >400 |

TABLE 1d (formula 1d)

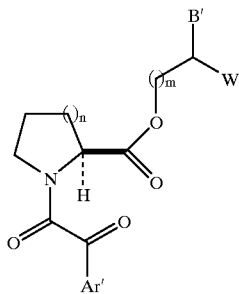

| B | U | J | K | $K_i$ (μM) |
|---|---|---|---|---|
| Benzyl | 4-methoxyphenyl | Methyl | S-Methyl | 80 |
| Benzyl | 4-methoxyphenyl | Methyl | S-Isopopyl | 30 |
| Benzyl | 3,4-Methylenedioxyphenyl | Methyl | S-Methyl | 50 |
| Benzyl | 3,4-Methylenedioxyphenyl | Hydrogen | S-Methyl | 60 |

TABLE 2

(formula II')

| Cpd. | n | m | B' | W | Ar' | $K_i$ (nM) |
|---|---|---|---|---|---|---|
| 2 | 1 | 0 | 3-(Pyridin-2-yl) propyl | 3-Phenylpropyl | 3,4,5-Trimethoxyphenyl | 95. |
| 3 | 2 | 0 | 3-Phenylpropyl | 3-Phenylpropyl | 3,4,5-Trimethoxyphenyl | 1. |
| 4 | 2 | 0 | 3-Phenoxyphenyl | 3-Phenylpropyl | 3,4,5-Trimethoxyphenyl | 220. |
| 5 | 2 | 0 | Phenyl | 3-Phenoxyphenyl | 3,4,5-Trimethoxyphenyl | 4,000. |
| 6 | 2 | 0 | Phenyl | 3-Phenylpropyl | 3,4,5-Trimethoxyphenyl | 80. |
| 7 | 2 | 0 | 2-(Pyridin-3-yl) ethyl | 3-Phenylpropyl | 3,4,5-Trimethoxyphenyl | 3. |
| 8 | 2 | 0 | E-3-[trans-(4-Hydroxycyclo-hexyl)]-2-methyl-eth-2-enyl | 3-Phenylpropyl | 3,4,5-Trimethoxyphenyl | 27. |
| 9 | 2 | 0 | 3-(Pyridin-3-yl)propyl | 3-Phenylpropyl | 3,4,5-Trimethoxyphenyl | 0.5 |
| 10 | 2 | 0 | Benzyl | 3-Phenylpropyl | 3,4,5-Trimethoxyphenyl | 32. |
| 11 | 2 | 0 | Benzyl | 3-(Indol-3-yl) propyl | 3,4,5-Trimethoxyphenyl | 24. |
| 12 | 2 | 0 | 2-Phenylethyl | 3-Phenylpropyl | 3,4,5-Trimethoxyphenyl | 83. |
| 13 | 2 | 0 | 2-(4-Methoxy-phenyl)ethyl | 3-Phenylpropyl | 3,4,5-Trimethoxyphenyl | 3.5 |
| 14 | 2 | 0 | 2-(4-Methoxy-phenyl)ethyl | 3-Phenylpropyl | Phenyl | 270. |
| 15 | 2 | 0 | 3-(N-Benzimidazolyl)propyl | 3-Phenylpropyl | 3,4,5-Trimethoxyphenyl | 5. |
| 16 | 2 | 1 | Benzyl | 2-Phenylethyl | 3,4,5-Trimethoxyphenyl | 57. |
| 17 | 2 | 0 | 3-(4-Methoxy-phenyl)propyl | 3-Phenylpropyl | 3,4,5-Trimethoxyphenyl | 3. |
| 18 | 2 | 0 | 3-(Pyridin-3-yl)-propyl | 3-Phenylpropyl | Phenyl | 56. |
| 19 | 2 | 0 | 3-(Pyridin-2-yl)-propyl | 3-Phenylpropyl | Phenyl | 50. |
| 20 | 2 | 0 | 3-(Pyridin-2-yl)-propyl | 3-Phenylpropyl | 3,4,5-Trimethoxyphenyl | 6.5 |
| 21 | 2 | 0 | 3-(Pyridin-2yl)-propyl | 3-Phenylpropyl | tert-Butyl | 36. |
| 22 | 2 | 0 | 3-(Pyridin-3-yl)-propyl-N-oxide | 3-Phenylpropyl | 3,4,5-Tdmethoxyphenyl | 7. |
| 23 | 2 | 0 | 3-IN-(7-Azaindolyl)-propyl | 3-Phenylpropyl | 3,4,5-Trimethoxyphenyl | 9. |
| 24 | 2 | 0 | 3-(Pyridin-3-yl)-propyl | 3-(4-Methoxy-phenyl)-propyl | 3,4,5-Trimethoxyphenyl | ND |
| 25 | 2 | 0 | 3-(N-Purinyl) propyl | 3-Phenylpropyl | 3,4,5-Trimethoxyphenyl | 2.2 |
| 26 | 2 | 0 | 3-(4-Hydroxy-methylphenyl) propyl | 3-Phenylpropyl | 3,4,5-Trimethoxyphenyl | 4. |
| 27 | 2 | 0 | 3-(Pyridin-3-yl)-propyl | 3-Phenylpropyl | 3-Benzyloxyphenyl | 15. |
| 28 | 2 | 0 | 3-(Pyridin-3-yl)-propyl | 3-Phenylpropyl | 3-Allyloxyphenyl | 11. |
| 29 | 2 | 0 | 3-(Pyridin-3-yl)-propyl | 3-Phenylpropyl | 3-Isopropoxyphenyl | 2. |

TABLE 2-continued (formula II')

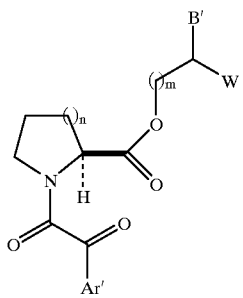

| Cpd. | n | m | B' | W | Ar' | $K_i$ (nM) |
|---|---|---|---|---|---|---|
| 30 | 2 | 0 | 3-(Thiophen-2-yl)-propyl | 3-Phenylpropyl | 3,4,5-Trimethoxyphenyl | 4. |
| 31 | 2 | 0 | 3-(4-Carboxyphenyl)propyl | 3-Phenylpropyl | 3,4,5-Trimethoxyphenyl | 2. |
| 32 | 2 | 0 | 3-Phenylbutyl | 3-Phenylpropyl | 3,4,5-Trimethoxyphenyl | 20. |
| 33 | 2 | 0 | 2-Hydroxymethylphenyl | 3-Phenylpropyl | 3,4,6-Trimethoxyphenyl | 89. |
| 34 | 2 | 0 | 2-Allyloxyphenyl | 3-Phenylpropyl | 3,4,5-Trimethoxyphenyl | 150. |
| 35 | 2 | 0 | 3-(3-Hydroxymethylphenyl) propyl | 3-Phenylpropyl | 3,4,5-Trimethoxyphenyl | 1. |
| 36 | 2 | 0 | 3-(3-Carboxyphenyl)propyl | 3-Phenylpropyl | 3,4,5-Trimethoxyphenyl | 4. |
| 37 | 2 | 0 | 3-Hydroxymethylphenyl | 3-Phenylpropyl | 3,4,5-Trimethoxyphenyl | 6.8 |
| 38 | 2 | 0 | 2-Hydroxyphenyl | 3-Phenylpropyl | 3,4,5-Trimethoxyphenyl | ND |
| 39 | 2 | 0 | Pyridin-3-yl | 3-Phenylpropyl | 3,4,5-Trimethoxyphenyl | ND |
| 40 | 2 | 0 | 3-(Thiopen-2-yl)-propyl | 4-Phenylbutyl | 3,4,5-Trimethoxyphenyl | 1,100. |
| 41 | 2 | 0 | 5-Phenylpentyl | 3-Phenylpropyl | 3,4,5-Trimethoxyphenyl | 45. |
| 42 | 2 | 0 | 3-Allyloxypropyl | 3-Phenylpropyl | 3,4,5-Trimethoxyphenyl | ND |
| 43 | 2 | 0 | 3-[4-(N,N-Dimethylamine-carbonyl)-phenyl] propyl | 3-Phenylpropyl | 3,4,5-Trimethoxyphenyl | 5. |
| 44 | 2 | 0 | 3-[4-(Morpholine-4-carbonyl)phenyl]-propyl | 3-Phenylpropyl | 3,4,5-Trimethoxyphenyl | 6. |
| 45 | 2 | 0 | 4-Alllyoxybutyl | 3-Phenylpropyl | 3,4,5-Trimethoxyphenyl | 7. |
| 46 | 2 | 0 | 3-Allyloxy-prop-1-ynyl | 3-Phenylpropyl | 3,4,5-Trimethoxyphenyl | 5. |
| 47 | 2 | 0 | 3-[4-(Piperidine-1-carbonyl)phenyl]-propyl | 3-Phenylpropyl | 3,4,5-Trimethoxyphenyl | 7. |
| 48 | 2 | 0 | 5-Allyloxynonyl | 3-Phenylpropyl | 3,4,5-Trimethoxyphenyl | ND |
| 49 | 2 | 0 | Methyl | 3,5-Bis(benzyloxy)phenyl | 3,4,5-Trimethoxyphenyl | 3,400. |
| 50 | 2 | 0 | 2-Allyloxyethyl | 3-Phenylpropyl | 3,4,5-Trimethoxyphenyl | 11. |
| 51 | 2 | 0 | 3-Allyloxy-(E)-prop-1-ynyl | 3-Phenylpropyl | 3,4,5-Trimethoxyphenyl | 2.8 |
| 52 | 2 | 0 | 3-[3-(Morpholine-4-carbonyl) phenyl]propyl | 3-Phenylpropyl | 3,4,5-Trimethoxyphenyl | 1.5 |
| 53 | 2 | 0 | Dec-9-enyl | 3-Phenylpropyl | 3,4,5-Trimethoxyphenyl | ND |
| 54 | 2 | 0 | 3-[4-(N-Benzyl-aminecarbonyl)-phenyl]propyl | 3-Phenylpropyl | 3,4,5-Trimethoxyphenyl | 1.6 |
| 55 | 2 | 0 | 3-[4-(Thiomorpholine-4-carbonyl) phenyl]propyl | 3-Phenylpropyl | 3,4,5-Trimethoxyphenyl | 2.4 |
| 56 | 2 | 0 | 3-(Morpholine-4-carbonyl)phenyl- | 3-Phenylpropyl | 3,4,5-Trimethoxyphenyl | 6.1 |
| 57 | 2 | 0 | 3-[4-(1-Methyl-piperazine-4-carbonyl)phenyl] propyl | 3-phenylpropyl | 3,4,5-Trimethoxyphenyl | 5.6 |
| 58 | 2 | 0 | 3-[4-(1-Benzyl-piperazine-4-carbonyl)phenyl] propyl | 3-Phenylpropyl | 3,4,5-Trimethoxyphenyl | 30. |
| 59 | 2 | 0 | 3-[3-(N-Benzyl-amine-carbonyl)phenylpropyl | 3-Phenylpropyl | 3,4,5-Trimethoxyphenyl | 40. |
| 60 | 2 | 0 | 3-[4-(N-Pyridin-2-ylaminecarbon-yl)-phenyl]propyl | 3-Phenylpropyl | 3,4,5-Trimethoxyphenyl | 2. |
| 61 | 2 | 0 | Pyridin-3-yl | 3-(Pyridin-3-yl)-propyl | 3,4,5-Trimethoxyphenyl | 10. |
| 62 | 2 | 0 | Prop-2-enyl | 3,4-Bis-(Pyridin-4-ylmethoxy)phenyl | 3,4,5-Trimethoxyphenyl | 62. |
| 63 | 2 | 0 | Pyridin-3-yl | 3-(Pyridin-4-yl-methoxy)phenyl | 3,4,5-Trimethoxyphenyl | 13. |
| 64 | 2 | 0 | 3-Phenylpropyl | 3-(Pyridin-4-yl-methoxy)phenyl | 3,4,5-Trimethoxyphenyl | 1.4 |
| 65 | 2 | 0 | 3-Phenylpropyl | 3,4-Bis-(Pyridin-4-ylmethoxy)phenyl | 3,4,5-Trimethoxyphenyl | 4.1 |
| 66 | 2 | 0 | Methyl | 3,4-Bis-(Pyridin-4-ylmethoxy)phenyl | 3,4,5-Trimethoxyphenyl | 35. |
| 67 | 2 | 0 | 3-Phenylpropyl | 2,3,4-Tris-(Pyridin-4-ylmethoxy)phenyl | 3,4,5-Trimethoxyphenyl | 46. |
| 68 | 2 | 0 | 3-Phenylpropyl | 3-(Morpholine-4- | 3,4,5-Trimethoxyphenyl | 2. |

TABLE 2-continued (formula II')

| Cpd. | n | m | B' | W | Ar' | $K_i$ (nM) |
|---|---|---|---|---|---|---|
| | | | | carbonyl)4-(Pyridin-4-ylmethoxy)phenyl | | |
| 69 | 2 | 0 | Methyl | 3,4,5-Tris-(Pyridin-4-ylmethoxy)phenyl | 3,4,5-Trimethoxyphenyl | 36. |
| 70 | 2 | 0 | 3-Phenylpropyl | 3,4,5-Tris-(Pyridin-4-ylmethoxy)phenyl | 3,4,5-Trimethoxyphenyl | 5. |
| 71 | 2 | 0 | Methyl | 3,5-Bis-(Pyridin-4-ylmethoxy)phenyl | 3,4,5-Trimethoxyphenyl | 14. |
| 72 | 2 | 0 | 3,5-Bis-(Pyridin-4-ylmethoxy) phenyl | Methyl | 3,4,5-Trimethoxyphenyl | 12. |
| 73 | 2 | 0 | Methyl | 3,5-Bis-(Pyridin-4-y(methoxy)4-Methyl-phenyl | 3,4,5-Trimethoxyphenyl | 36. |
| 74 | 2 | 0 | Ethyl | 3,4,5-Tris-(Pyridin-4-ylmethoxy)phenyl | 3,4,5-Trimethoxyphenyl | 18. |
| 75 | 2 | 0 | 3,4,5-Tris-(Pyridin-4-yl-methoxy)phenyl | Ethyl | 3,4,5-Trimethoxyphenyl | 12. |
| 76 | 2 | 0 | Prop-2-enyl | 3,4,5-Tris-(Pyridin-4-ylmethoxy)phenyl | 3,4,5-Trimethoxyphenyl | 14. |
| 77 | 2 | 0 | Methyl | 3,4,6-Tris-(Pyridin-4-ylmethoxy)phenyl | 3,4-Dimethoxyphenyl | 24. |
| 78 | 2 | 0 | Ethenyl | 3,4,5-Tris-(Pyridin-4-ylmethoxy)phenyl | 3,4,5-Trimethoxyphenyl | 73. |
| 79 | 2 | 0 | 3,4,5-Tris-(Pyridin-4-ylmethoxy)phenyl | Ethenyl | 3,4,5-Trimethoxyphenyl | 2.3 |
| 80 | 2 | 0 | Propyl | 3,4,5-Tris-(Pyridin-4-ylmethoxy)phenyl | 3,4,5-Trimethoxyphenyl | 17. |
| 81 | 2 | 0 | 3,4,5-Tris-(Pyridin-4-ylmethoxy)phenyl | Propyl | 3,4,5-Trimethoxyphenyl | 5. |
| 82 | 2 | 0 | Methyl | 3,4,5-Tris-(Thiophen-3-ylmethoxy)phenyl | 3,4,5-Trimethoxyphenyl | >5000 |
| 83 | 2 | 0 | 3,4,5-Tris-(Thio-phen-3-ylmethoxy)-phenyl | Methyl | 3,4,5-Trimethoxyphenyl | >1000 |
| 84 | 2 | 0 | Methyl | 2-Isopropoxy-3,4-Bis-(Pyridin-4-ylmethoxy)-phenyl | 3,4,5-Trimethoxyphenyl | 54. |
| 85 | 2 | 0 | 2-Isopropoxy-3,4-Bis-(Pyridin-4-yl-methoxy) phenyl | Methyl | 3,4,5-Trimethoxyphenyl | 3.5 |
| 86 | 1 | 0 | Methyl | 3,4,5-Tris-(Pyridin-4-ylmethoxy)phenyl | 3,4,5-Trimethoxyphenyl | 280. |
| 87 | 1 | 0 | 3,4,5-Tris,-(Pyridin-4-ylmethoxy)phenyl | Methyl | 3,4,5-Trimethoxyphenyl | 360. |
| 88 | 2 | 0 | Methyl | 3,4,5-Tris-(Pyrimidin-4-ylmethoxy)phenyl | 3,4,5-Trimethoxyphenyl | 19. |
| 89 | 2 | 0 | Benzyloxymethyl | Benzyloxyphenyl | 3,4,5-Trimethoxyphenyl | 5. |
| 90 | 2 | 0 | Methyl | 3,4,5-Tris-(Benzyloxy)phenyl | 3,4,5-Trimethoxyphenyl | 2,600. |
| 91 | 2 | 0 | 3-Phenylpropyl | 3-(Pyridin-3-yl-carbonyl)phenyl | 3,4,5-Trimethoxyphenyl | 24. |
| 92 | 2 | 0 | 3-(Pyridin-3-yl-carbonyl)phenyl | 3-Phenylpropyl | 3,4,5-Trimethoxyphenyl | 9. |
| 93 | 2 | 0 | 3-Phenylpropyl | 3-(Pyridin-4-yl-methoxy)phenyl | 3,4-Dimethoxyphenyl | 7.5 |
| 94 | 2 | 0 | 3-Phenylpropyl | 3-(Pyridin-4-yl-carbonyl)phenyl | 4-Benzyloxy-3,5-Di-methoxyphenyl | 25. |
| 95 | 2 | 0 | 3-Phenylpropyl | 3-(Pyridin-4-yl-carbonyl)phenyl | 4-Allyloxy-3,5-Di-methoxyphenyl | 3.6 |
| 96 | 2 | 0 | 3-Phenylpropyl | 3-(Pyridin-4-yl-carbonyl)phenyl | 3-Benzyloxy-4-methoxyphenyl | 25. |

TABLE 2-continued (formula II')

[Chemical structure of formula II' showing a pyrrolidine ring with substituents B', W, and Ar']

| Cpd. | n | m | B' | W | Ar' | $K_i$ (nM) |
|---|---|---|---|---|---|---|
| 97 | 2 | 0 | 3-Phenylpropyl | 3-(Pyridin-4-yl-carbonyl)phenyl | 3-Allyloxy-4-methoxyphenyl | 17. |
| 98 | 2 | 0 | 3-Phenylpropyl | 3-(Pyridin-4-yl-carbonyl)phenyl | 3-[3-Phenyl-(E)-prop-2-enyl]-4-methoxyphenyl | 380. |
| 99 | 2 | 0 | 3-Phenylpropyl | 4-(Pyridin-4-yl-carbonyl)phenyl | 4-Benzyloxy-3,5-Di-methoxyphenyl | 15,000. |
| 100 | 2 | 0 | 3-Phenylpropyl | 4-(Pyridin-4-yl-carbonyl)phenyl | 3-Benzyloxy-4-methoxyphenyl | >5000 |
| 101 | 2 | 0 | 3-Phenylpropyl | 3-(Pyridin-4-yl-carbonyl)phenyl | 3,4,5-Trimethoxyphenyl | ND |
| 102 | 2 | 0 | 3-Phenylpropyl | 3-(Pyridin-4-yl-carbonyl)phenyl | 3,4-Dimethoxyphenyl | ND |
| 103 | 2 | 0 | 3-Phenylpropyl | Phenyl | 3-Benzyloxy-4-methoxyphenyl | 24,000. |
| 104 | 2 | 0 | 3-Phenylpropyl | Phenyl | 4-Benzyloxy-3,5-Dimethoxyphenyl | 1,700. |
| 105 | 1 | 0 | 3-(Pyridin-3-yl)-propyl | 3-Phenylpropyl | tert-Butyl | 340. |
| 106 | 2 | 0 | 3-(Pyridin-3-yl)-propyl | 3-(Pyridin-3-yl)-propyl | 3,4,5-Trimethoxyphenyl | 3.7 |
| 107 | 1 | 0 | Benyloxymethyl | Benzyloxymethyl | 3,4,5-Trimethoxyphenyl | 75,000. |
| 108 | 1 | 0 | 3-(Pyridin-3-yl)-propyl | 3-(Pyridin-3-yl)-propyl | 3,4,5-Trimethoxyphenyl | 89. |
| 109 | 2 | 0 | 3-(Pyridin-3-yl)-propyl | 3-(Pyridin-3-yl)-propyl | Isopropyl | 1,500. |
| 110 | 2 | 0 | 3-(Pyridin-3-yl)- | 3-(Pyridin-3-yl)- | Thiophen-2-yl | ND |
| 111 | 2 | 0 | 3-(Pyridin-3-yl)-propyl | 3-(Pyridin-3-yl)-propyl | 3,4-Methylenedioxy-phenyl | ND |
| 112 | 2 | 0 | 3-(Pyridin-3-yl)-prop-2-ynyl | 3-(Pyridin-3-yl)-prop-2-ynyl | 3,4-Methylenedioxy phenyl | ND |
| 113 | 2 | 0 | 3-(Pyridin-3-yl)-prop-2-ynyl | 3-(Pyridin-3-yl)-prop-2-ynyl | 3,4,5-Trimethoxyphenyl | ND |
| 114 | 2 | 0 | 3-(Pyridin-2-yl)-propyl | 3-(Pyridin-2-yl)-propyl | 3,4,5-Trimethoxyphenyl | ND |
| 115 | 2 | 0 | Isopropyl | 3,4,5-Tris-(Pyridin-4-ylmethoxy)phenyl | 3,4,5-Trimethoxyphenyl | 0.39 |
| 116 | 2 | 0 | 3,4,5-Tris-(Pyridin-4-ylmethoxy)phenyl | Isopropyl | 3,4,5-Trimethoxyphenyl | 13. |
| 118 | 2 | 0 | 3,4,5-Tris-(Pyridin-4-ylmethoxy)phenyl | Prop-2-enyl | 3,4,5-Trimethoxyphenyl | 12. |

EXAMPLE 2

Assay of Neurite Outgrowth in PC12 Cultures

In order to directly determine the neurotrophic activity of the FKBP12 binding compounds utilized in this invention, the assay described by W. E. Lyons et al., *Proc. Natl. Acad. Sci. USA*, 91, pp. 3191–95 (1994) is carried out.

PC12 rat pheochromocytoma cells are maintained at 37° C. and 5% $CO_2$ in Dulbecco's modified Eagle's medium (DMEM) supplemented with 10% heat-inactivated horse serum (HS) and 5% heat-inactivated fetal bovine serum (FBS). The cells are then plated at $10^5$ per 35 mm culture well coated with 5 µg/cm² rat tail collagen and allowed to attach. The medium is then replaced with DMEM+2% HS and 1% FBS, NGF (1–100 ng/ml) and varying concentrations of an FKBP12 binding compound (0.1 nM–10 µM). Control cultures are administered NGF without FKBP12 binding compound.

The FKBP12 binding compounds utilized in this invention cause a significant increase in neurite outgrowth over control cultures.

EXAMPLE 3

Assay of Neurite Outgrowth in Dorsal Root Ganalion Culture

Another way to directly determine the neurotrophic activity of the FKBP12 binding compounds utilized in this invention is the dorsal root ganglion culture assay also described by W. E. Lyons et al., *Proc. Natl. Acad. Sci. USA*, 91, pp. 3191–95 (1994).

In this assay, dorsal root ganglia are dissected from 16 day rat embryos and cultured in collagen-coated 35 mm dishes with N2 medium at 37° C. in a 15% $CO_2$ environment. Sensory ganglia are then treated with various concentrations of NGF (0–100 ng/ml) and an FKB12 binding compound (0.1 nM–10 µM). Ganglia are observed every two days under a phase contrast microscope and axon lengths are measured. Control cultures either lack FKBP12 binding compound or lack FKBP12 binding compound and NGF.

The FKBP12 binding compounds utilized in this invention cause a significant increase in neurite outgrowth over control cultures which lack such compounds in both the presence and absence of NGF.

While I have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

I claim:

1. A method for stimulating neurite growth in nerve cells comprising the step of contacting said nerve cells with a composition comprising a neurotrophic amount of a compound having the formula (II):

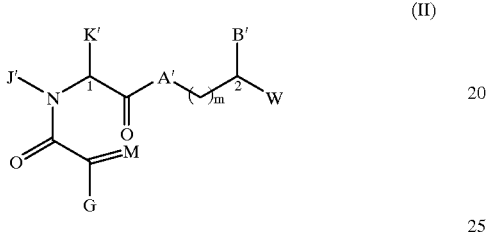

(II)

and pharmaceutically acceptable derivatives thereof, wherein A' is CH$_2$, oxygen, NH or N-(C1–C4 alkyl);

B' and W are independently:

(i) hydrogen, Ar', (C1–C10)-straight or branched alkyl, (C2–C10)-straight or branched alkenyl or alkynyl, (C5–C7)-cycloalkyl-substituted (C1–C6)-straight or branched alkyl, (C5–C7)-cycloalkyl-substituted (C2–C6)-straight or branched alkenyl or alkynyl, (C5–C7)-cycloalkenyl-substituted (C1–C6)-straight or branched alkyl, (C5–C7)-cycloalkenyl-substituted (C2–C6)-straight or branched alkenyl or alkynyl, Ar'-substituted-(C1–C6)-straight or branched alkyl, or Ar'-substituted-(C2–C6)-straight or branched alkenyl or alkynyl; wherein, in each case, any one of the CH$_2$ groups of said alkyl, alkenyl or alkynyl chains may be optionally replaced by a heteroatom selected from the group consisting of O, S, SO, SO$_2$, N, and NR, wherein R is selected from the group consisting of hydrogen; (C1–C4)-straight or branched alkyl; (C2–C4)-straight or branched alkenyl or alkynyl; (C1–C4) bridging alkyl, wherein a bridge is formed between the nitrogen and a carbon atom of said heteroatom-containing chain to form a ring, and wherein said ring is optionally fused to an Ar' group; or

(ii)

wherein Q' is hydrogen, (C1–C6)-straight or branched alkyl or (C2–C6)-straight or branched alkenyl or alkynyl; and T' is Ar' or a 5–7 membered cycloalkyl ring with substituents at positions 3 and 4, said substituents being independently selected from oxo, hydrogen, hydroxyl, O-(C1–C4)-alkyl, or O-(C2–C4)-alkenyl;

wherein Ar' is selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl; and wherein Ar' optionally contains one to three substituents which are independently selected from halogen, hydroxyl, hydroxymethyl, nitro, trifluoromethyl, trifluoromethoxy, (C1–C6)-straight or branched alkyl, (C2–C6)-straight or branched alkenyl, O-[(C1–C4)-straight or branched alkyl], O-[(C2–C4)-straight or branched alkenyl], O-benzyl, O-phenyl, 1,2-methylenedioxy, amino, carboxyl, N-[(C1–C5)-straight or branched alkyl or (C2–C5)-straight or branched alkenyl]-carboxamide, N,N-di-[(C1–C5)-straight or branched alkyl or (C2–C5)-straight or branched alkenyl] carboxamide, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and q is 0–2;

G is U';

M is either oxygen or CH—U'; provided that if G is hydrogen, then M is CH—U' or if M is oxygen, then U' is not hydrogen;

wherein U' is hydrogen, O-[(C1–C4)-straight or branched alkyl], O-[(C2–C4)straight or branched alkenyl], (C1–C6)-straight or branched alkyl, (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]-Y or Y;

wherein Y is selected from the group consisting of phenyl, 1-naphthyl, 2-naphthyl, indenyl, azulenyl, fluorenyl, anthracenyl, 2-pyrrolinyl, 3-pyrrolinyl, pyrrolidinyl, 1,3-dioxolyl, 2-imidazolinyl, imidazolidinyl, 2H-pyranyl, 4H-pyranyl, piperidyl, 1,4-dioxanyl, morpholinyl, 1,4-dithianyl, thiomorpholinyl, piperazinyl, quinuclidinyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl; and wherein Y optionally contains one to three substituents which are independently selected from halogen, hydroxyl, hydroxymethyl, nitro, trifluoromethyl, trifluoromethoxy, (C1–C6)-straight or branched alkyl, (C2–C6)-straight or branched alkenyl, O-[(C1–C4)-straight or branched alkyl], O-[(C2–C4)-straight or branched alkenyl], O-benzyl, O-phenyl, 1,2-methylenedioxy, amino, or carboxyl;

J' is hydrogen, (C1–C2) alkyl or benzyl;

K' is (C1–C4)-straight or branched alkyl, benzyl or cyclohexylmethyl; or J' and K' are taken together with the nitrogen atom and the carbon atom to which they are respectively bound to form a 7-membered heterocyclic ring optionally containing a heteroatom selected from the group consisting of O, S, SO and SO$_2$ or a 5–6 membered heterocyclic ring containing a heteroatom selected from the group consisting of O, S, SO and SO$_2$; and m is 0–3.

2. A method for stimulating neurite growth in nerve cells comprising the step of contacting said nerve cells with a composition comprising a neurotrophic amount of a compound having the formula (II):

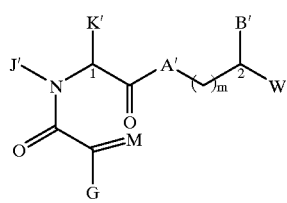

(II)

and pharmaceutically acceptable derivatives thereof, wherein A', B', G, M, W, Ar' and its optional substituents, X, Y and its optional substituents, R, T', Q', U', q and m are as defined in claim 1; and J' and K' are taken together with the nitrogen atom and the carbon atom to which they are respectively bound to form a 6-membered heterocyclic ring;

provided that when m is 0, A and M are oxygen, G is 1,1-dimethyl-1-propyl, and W is 2-phenylethyl, then B' is not 1,1-dimethyl-1-prop-2-enyl, phenyl, cylcohexyl, or 3-(N,N-diallyl)benzamide; and when m is 0, A and M are oxygen, G is tert-butyl, and W is 2-(3',4',5'-trimethoxyphenyl)ethyl, then B' is not phenyl.

3. A method for stimulating neurite growth in nerve cells comprising the step of contacting said nerve cells with a composition comprising a neurotrophic amount of a compound having the formula (II):

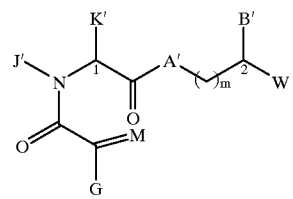

(II)

and pharmaceutically acceptable derivatives thereof, wherein A', B', G, M, W, Ar' and its optional substituents, X, Y and its optional substituents, R, T', Q', U', q and m are as defined in claim 1; and J' and K' are taken together with the nitrogen atom and the carbon atom to which they are respectively bound to form a 5–6 membered heterocyclic ring;

provided at least one of B' or W is independently selected from the group consisting of (C2–C10)-straight or branched alkynyl; (C5–C7)-cycloalkyl substituted (C2–C6)-straight or branched alkynyl; (C5–C7)-cycloalkenyl substituted (C2–C6)-straight or branched alkynyl; and Ar' substituted (C2–C6)-straight or branched alkynyl; and provided that if G is hydrogen, then M is CH—U' or if M is oxygen, then G is not hydrogen.

4. A method for stimulating neurite growth in nerve cells comprising the step of contacting said nerve cells with a composition comprising a neurotrophic amount of a compound having the formula (II):

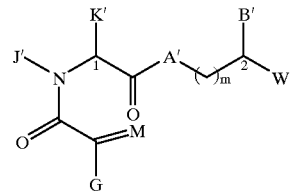

(II)

and pharmaceutically acceptable derivatives thereof, wherein A', B', G, M, W, Ar', X, Y and its optional substituents, R, T', Q', U', q and m are as defined in claim 1;

Ar' contains one to three substituents which are independently selected from the group consisting of N-[(C1–C5)-straight or branched alkyl or (C2–C5)-straight or branched alkenyl] carboxamide, N,N-di-[(C1–C5)-straight or branched alkyl or (C2–C5)-straight or branched alkeny)]carboxamide, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

J' and K' are taken together with the nitrogen atom and the carbon atom to which they are respectively bound to form a 5–6 membered heterocyclic ring;

provided that at least one of B' or W is Ar', Ar'-substituted (C1–C6)-straight or branched alkyl, and Ar'-substituted (C2–C6)-straight or branched alkenyl or alkynyl; and provided that if G is hydrogen, then M is CH—U' or if M is oxygen, then G is not hydrogen.

5. A method for stimulating neurite growth in nerve cells comprising the step of contacting said nerve cells with a composition comprising a neurotrophic amount of a compound having the formula (II):

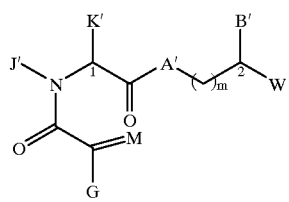
(II)

and pharmaceutically acceptable derivatives thereof,
wherein A', B', G, W, Ar' and its optional substituents and its optional substituents, X, Y, R, T', Q', U', q and m are as defined in claim 1;
M is CH—U'; and
J' and K' are taken together with the nitrogen atom and the carbon atom to which they are respectively bound to form a 5–6 membered heterocyclic ring.

6. A method for stimulating neurite growth in nerve cells comprising the step of contacting said nerve cells with a composition comprising a neurotrophic amount of a compound having the formula (II):

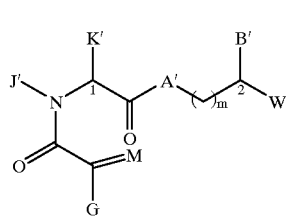
(II)

and pharmaceutically acceptable derivatives thereof, wherein A', B', G, W, Ar' and its optional substituents, M, X, Y and its optional substituents, R, T', Q', U', q and m are as defined in claim 1; and
J' and K' are taken together with the nitrogen atom and the carbon atom to which they are respectively bound to form a 5-membered heterocyclic ring;
provided that if G is hydrogen, then M is CH—U' or if M is oxygen, then G is not hydrogen; and
provided that when:
M is oxygen;
A is oxygen, NH or N-(C1–C4 alkyl);
G is (C1–C6)-straight or branched alkyl, (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, or Y; and
Y is 1-napthyl, 2-napthyl, indolyl, 2-furyl, 3-furyl, thiazolyl, 2-thienyl, 3-thienyl, 2-pyridyl, 3-pyridyl, 4-pyridyl or phenyl;
then $(CH_2)_m$, B' and W, taken together, do not form:
i) substituted or unsubstituted indolyl, 2-furyl, 3-furyl, thiazolyl, 2-thienyl, 3-thienyl, 2-pyridyl, 3-pyridyl, 4-pyridyl or phenyl;
ii) an alkyl or alkenyl chain substituted with substituted or unsubstituted indolyl, 2-furyl, 3-furyl, thiazolyl, 2-thienyl, 3-thienyl, 2-pyridyl, 3-pyridyl, 4-pyridyl or phenyl; or
iii) an alkyl or alkenyl chain substituted with (C5–C7)-cycloalkyl.

7. The method according to claim 1, wherein in said compound with affinity for FKBP12:
B' and W are independently:
(i) hydrogen, Ar', (C1–C10)-straight or branched alkyl, (C2–C10)-straight or branched alkenyl or alkynyl, (C5–C7)-cycloalkyl substituted (C1–C6)-straight or branched alkyl, (C2–C6)-straight or branched alkenyl or alkynyl, (C5–C7)-cycloalkenyl substituted (C1–C6)-straight or branched alkyl, (C2–C6)-straight or branched alkenyl or alkynyl, or Ar' substituted (C1–C6)-straight or branched alkyl, (C2–C6)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$; or

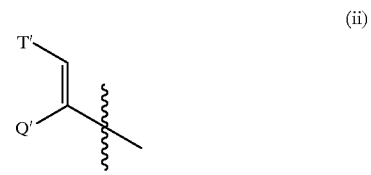
(ii)

Ar' may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O-[(C1–C4)-straight or branched alkyl], O-[(C2–C4)-straight or branched alkenyl], O-benzyl, O-phenyl, 1,2-methylenedioxy, amino and carboxyl; and
Y is selected from the group consisting of phenyl, 1-naphthyl, 2-naphthyl, indenyl, azulenyl, fluorenyl, anthracenyl and heterocyclic aromatic groups as defined for Ar above.

8. The method according to claim 1, wherein in said compound with affinity for FKBP12:
at least one of B' or W is independently selected from the group consisting of (C2–C10)-straight or branched alkynyl; (C5–C7)-cycloalkyl substituted (C2–C6)-straight or branched alkynyl; (C5–C7)-cycloalkenyl substituted (C2–C6)-straight or branched alkynyl; and Ar' substituted (C2–C6)-straight or branched alkynyl.

9. The method according to claim 1, wherein in said compound with affinity for FKBP12:
at least one of B' or W is independently represented by the formula —$(CH_2)_r$—(Z)—$(CH_2)_s$—Ar', wherein:
Z is independently selected from the group consisting of $CH_2$, O, S, SO, $SO_2$, N, and NR;
r is 0–4; and
s is 0–1.

10. The method according to claim 1, wherein in said compound with affinity for FKBP12:
at least one of B' or W is independently selected from the group consisting of Ar', Ar'-substituted (C1–C6)-straight or branched alkyl, and Ar'-substituted (C2–C6)-straight or branched alkenyl or alkynyl; and wherein Ar' is substituted with one to three substituents which are independently selected from the group consisting of N-(straight or branched (C1–C5)-alkyl or (C2–C5)-alkenyl) carboxamides, N,N-di-(straight or branched (C1–C5)-alkyl or (C2–C5)-alkenyl) carboxamides, N-morpholinocarboxamide, N-benzylcarboxamide, N-thiomorpholinocarboxamide, N-picolinoylcarboxamide, O—X, $CH_2$—$(CH_2)_q$—X, O—$(CH_2)_q$—X, $(CH_2)_q$—O—X, and CH=CH—X.

11. The method according to any one of claims 1 to 6, wherein said method is used to treat a patient who is suffering from or has suffered from Alzheimer's disease, Parkinson's disease, ALS, stroke and ischemia associated with stroke, neural paropathy, other neural degenerative diseases, motor neuron diseases, sciatic crush, spinal cord injuries or facial nerve crush.

\* \* \* \* \*

UNITED STATES PATENT AND TRADEMARK OFFICE
CERTIFICATE OF CORRECTION

PATENT NO. : 6,037,370
DATED : March 14, 2000
INVENTOR(S) : David M. Armistead

Page 1 of 1

It is certified that error appears in the above-identified patent and that said Letters Patent is hereby corrected as shown below:

On title page, item 56 References Cited in the first occurrence of "W.E. Lyons" replace "gaglia" with --ganglia--.

Column 11, line 14, replace "is" with --are--.

Column 17, Table 2, Compound 22 replace "Tdmethoyphenyl" with --Trimethoxyphenyl--.

Column 24, line 50, replace "Ganalion" with --Ganglion --.

Column 25, line 53, delete "(ii)".

Column 28, line 52, replace "alkeny) ]" with --alkenyl]--.

Column 29, line 15, delete "and its optional substituents"

Signed and Sealed this

Fifth Day of June, 2001

*Attest:*

*Attesting Officer*

NICHOLAS P. GODICI

*Acting Director of the United States Patent and Trademark Office*